United States Patent
Makihira et al.

(10) Patent No.: US 9,138,141 B2
(45) Date of Patent: Sep. 22, 2015

(54) OPHTHALMOLOGIC APPARATUS

(71) Applicant: CANON KABUSHIKI KAISHA, Tokyo (JP)

(72) Inventors: Tomoyuki Makihira, Tokyo (JP); Kazuhide Miyata, Yokohama (JP); Makoto Sato, Tokyo (JP); Yoshihiko Iwase, Kyoto (JP); Kazuro Yamada, Kawasaki (JP); Ritsuya Tomita, Kawasaki (JP); Daisuke Kibe, Chigasaki (JP); Hiroyuki Shinbata, Tama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/851,846

(22) Filed: Mar. 27, 2013

(65) Prior Publication Data

US 2013/0258284 A1    Oct. 3, 2013

(30) Foreign Application Priority Data

Mar. 30, 2012 (JP) ................................ 2012-082687

(51) Int. Cl.
| | |
|---|---|
| A61B 3/14 | (2006.01) |
| A61B 3/00 | (2006.01) |
| A61B 3/10 | (2006.01) |

(52) U.S. Cl.
CPC ................ *A61B 3/14* (2013.01); *A61B 3/0058* (2013.01)

(58) Field of Classification Search
CPC ............... A61B 3/00; A61B 3/10; A61B 3/14
USPC .................. 351/206, 205, 221, 210, 200, 246
See application file for complete search history.

(56) References Cited

U.S. PATENT DOCUMENTS

| | | |
|---|---|---|
| 5,321,501 A | 6/1994 | Swanson et al. |
| 8,226,233 B2 | 7/2012 | Sugita et al. |
| 2007/0070295 A1 | 3/2007 | Tsukada et al. |
| 2008/0084538 A1* | 4/2008 | Maeda et al. ................. 351/206 |
| 2008/0100612 A1* | 5/2008 | Dastmalchi et al. .......... 345/418 |
| 2008/0151187 A1 | 6/2008 | Tsukada et al. |
| 2010/0189817 A1 | 7/2010 | Krueger et al. |
| 2010/0238403 A1* | 9/2010 | Kobayashi et al. ........... 351/206 |
| 2012/0121158 A1 | 5/2012 | Sekine et al. |
| 2012/0194783 A1 | 8/2012 | Wei et al. |
| 2012/0281184 A1 | 11/2012 | Tori et al. |

FOREIGN PATENT DOCUMENTS

| | | |
|---|---|---|
| JP | 2007-117714 A | 5/2007 |
| WO | WO 2011122007 A2 * | 10/2011 |

OTHER PUBLICATIONS

U.S. Appl. No. 13/851,882, filed Mar. 27, 2013, Yoshihiko Iwase.

* cited by examiner

*Primary Examiner* — Dawayne A Pinkney
(74) *Attorney, Agent, or Firm* — Canon USA, Inc., IP Division

(57) ABSTRACT

An ophthalmologic apparatus includes an irradiation optical system configured to guide light emitted from a light source to the subject's eye, a control unit configured to sweep a wavelength of light emitted from the light source, an imaging optical system configured to guide to an imaging unit a return beam from the subject's eye of light swept by the control unit, a tomographic image acquisition unit configured to acquire a tomographic image of the subject's eye based on an output from the imaging unit, a fundus image acquisition unit configured to acquire a fundus image of the subject's eye, and a display control unit configured to display the fundus image on a first area in a display unit and display the tomographic image on a second display area which is positioned above or below the first area and is wider in a horizontal direction as compared to the first area.

19 Claims, 12 Drawing Sheets

OPHTHALMOLOGIC APPARATUS

BACKGROUND OF THE INVENTION

1. Field of the Invention

The present invention relates to an ophthalmologic apparatus.

2. Description of the Related Art

An optical coherence tomography (OCT) imaging apparatus such as an OCT allows three-dimensional observation of a state within retinal layers. Such an optical coherence tomography imaging apparatus is recently attracting attention as being useful in more accurately diagnosing diseases.

A time domain OCT (TD-OCT) is a type of OCT in which a broad spectrum light source is combined with a Michelson interferometer. The TD-OCT scans a delay in a reference arm to measure the interference light generated by a backscattered light of a signal arm and the light from the reference arm interfering with each other, and acquires information on depth resolution. However, high-speed image acquisition is difficult when such TD-OCT is used. In contrast, a spectral domain OCT (SD-OCT) in which a spectroscope acquires an interferogram by employing the broad spectrum light source is capable of capturing the image at higher speed. Further, U.S. Pat. No. 5,321,501 discusses a swept source OCT (SS-OCT) in which a single channel light detection device measures spectral interference by employing a high-speed swept light source as the light source.

Since the spectroscope in the SD-OCT disperses the interference light using a diffraction grating, crosstalk by the interference light tends to occur between adjacent pixels of a line sensor. Further, the interference light from a reflection surface positioned at a depth position $Z=Z0$ vibrates at a frequency of $Z0/\pi$ with respect to a wave number k. A vibration frequency of the interference light thus increases as $Z0$ increases (i.e., the reflection surface moves away from a coherence gate position), so that the effect of the crosstalk by the interference light between the adjacent pixels in the line sensor increases. As a result, when the SD-OCT performs imaging at a deeper position, sensitivity is lowered. In contrast, the SS-OCT which does not use the spectroscope is advantageous as compared to the SD-OCT in being capable of capturing the tomographic image at a deeper position.

Furthermore, in the SD-OCT, there is a loss of interference light caused by the diffraction grating in the spectroscope. On the other hand, the SS-OCT which does not include the spectroscope is capable of easily improving the sensitivity by performing differential detection of the interference light. The SS-OCT is thus capable of performing high-speed processing at the same level of sensitivity as the SD-OCT, and of capturing a tomographic image of a wide viewing angle employing the high-speed capability.

Moreover, Japanese Patent Application Laid-Open No. 2007-117714 discusses the SD-OCT which displays the tomographic image and the fundus image side by side in a horizontal direction of a display area on the display unit.

However, if the tomographic image of a wide viewing angle acquired by the SS-OCT is displayed side by side with the fundus image, it becomes necessary to display a reduced tomographic image, or display a portion of the tomographic image due to the limit on the size of the display area. The tomographic image captured by the SS-OCT thus cannot be efficiently displayed.

SUMMARY OF THE INVENTION

The present invention is directed to efficiently displaying the tomographic image of a wide viewing angle captured by the SS-OCT. Such operational advantage is derived by each of configurations illustrated in exemplary embodiments of the present invention to be described below, and operational advantages that are not acquirable by conventional techniques are also included in the present invention.

According to an aspect of the present invention, an ophthalmologic apparatus includes an irradiation optical system configured to guide light emitted from a light source to a subject's eye, a control unit configured to sweep a wavelength of light emitted from the light source, an imaging optical system configured to guide to an imaging unit a return beam from the subject's eye of light swept by the control unit, a tomographic image acquisition unit configured to acquire a tomographic image of the subject's eye based on an output from the imaging unit, a fundus image acquisition unit configured to acquire a fundus image of the subject's eye, and a display control unit configured to display the fundus image on a first area in a display unit and display the tomographic image on a second display area in the display unit which is positioned above or below the first area and is wider in a horizontal direction as compared to the first area.

According to the present invention, the tomographic image of a wide viewing angle can be efficiently displayed.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

The apparatus according to the present invention is applicable to a subject such as the subject's eye, the skin, and internal organs. Further, the apparatus according to the present invention is an ophthalmologic apparatus or an endoscope. The ophthalmologic apparatus according to the first exemplary embodiment, which is an example of the present invention, will be described in detail below with reference to the drawings.

<Configuration of the Apparatus>

Figure 1:
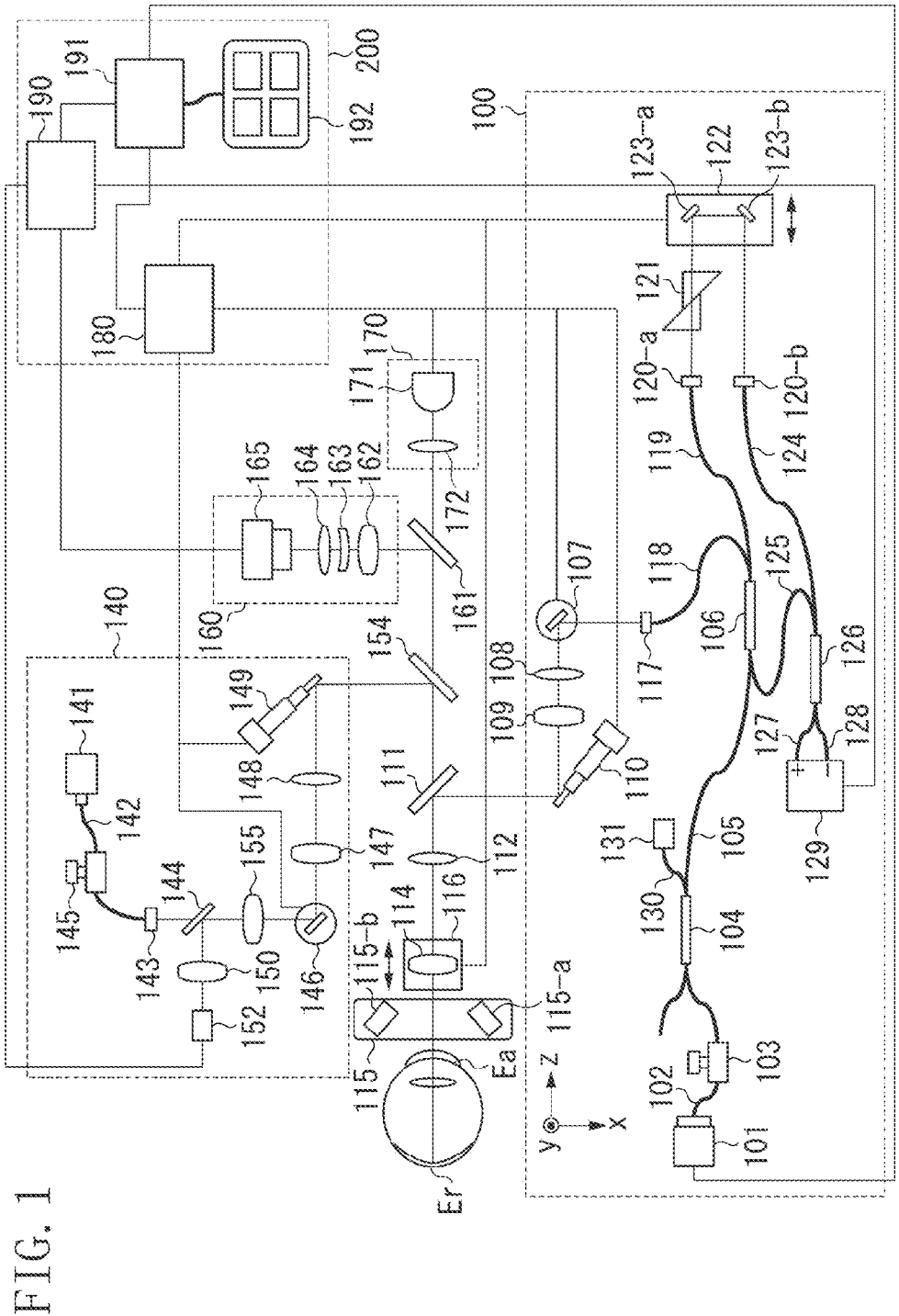
FIG. 1 is a schematic diagram illustrating an example of a configuration of an ophthalmologic apparatus according to a first exemplary embodiment of the present invention.

FIG. 1 is a schematic diagram illustrating an example of a configuration of the ophthalmologic apparatus according to the present exemplary embodiment.

Referring to FIG. 1, the ophthalmologic apparatus includes a SS-OCT (or may be simply referred to as OCT) 100, a scanning laser ophthalmoscope (SLO) 140, an anterior segment imaging unit 160, an internal fixation lamp 170, and a control unit 200.

The ophthalmologic apparatus is aligned by lighting and causing the subject's eye to gaze at the internal fixation lamp 170, and using the image of the anterior segment of the subject captured by the anterior segment imaging unit 160. After completing the alignment, the OCT 100 and the SLO 140 perform imaging of the fundus.

<Configuration of the OCT 100>

An example of the configuration of the OCT 100 will be described below.

The OCT 100 is an example of the tomographic image acquisition unit configured to acquire the tomographic image of the subject's eye.

A light source 101 which is a variable wavelength light source emits light having a central wavelength of, e.g., 1040 nm and a bandwidth of 100 nm. A control unit 191 controls the wavelength of the light emitted from the light source 101. More specifically, when the OCT 100 captures the tomographic image, the control unit 191 sweeps the wavelength of the light emitted from the light source 101. The control unit 191 thus is an example of a control unit configured to sweep the wavelength of the light emitted from the light source.

The light emitted from the light source 101 is guided by a fiber 102 and a polarization controller 103 to a fiber coupler 104, and is divided to be guided to a fiber 130 for measuring a light amount, and a fiber 105 for performing OCT measurement. A power meter (PM) 131 measures the power of the light guided to the fiber 130. The light guided to the fiber 105 is then guided to a second fiber coupler 106, which splits the light into a measuring beam (also referred to as an OCT measuring beam) and a reference beam.

The polarization controller 103 adjusts a polarization state of the beam emitted from the light source 101, and adjusts the beam to a linearly-polarized beam. A branching ratio of the fiber coupler 104 is 99:1, and the branching ratio of the fiber coupler 106 is 90 (reference beam):10 (measuring beam). The branching ratios are not limited thereto, and may be other values.

The measuring beam acquired by the fiber coupler 106 is output from a collimator 117 via a fiber 118 as a parallel beam. The output measuring beam reaches a dichroic mirror 111 via an X scanner 107 and lenses 108 and 109, and a Y scanner 110. The X scanner 107 includes a galvano mirror that scans a fundus Er with the measuring beam in a horizontal direction (i.e., in a vertical direction with respect to the drawing), and the Y scanner 110 includes a galvano mirror that scans the fundus Er with the measuring beam in a vertical direction (i.e., in a depth direction with respect to the drawing). The X scanner 107 and the Y scanner 110 are controlled by a drive control unit 180, and are capable of scanning the fundus Er with the measuring beam in a desired range. The dichroic mirror 111 reflects light having wavelengths of 950 nm to 1100 nm, and transmits light of other wavelengths.

The measuring beam reflected off the dichroic mirror 111 reaches via a lens 112 a focus lens 114 mounted on a stage 116. The focus lens 114 focuses the measuring beam on the retinal layers in the fundus Er via an anterior segment Ea of the subject's eye. The optical system from the light source 101 to the subject's eye thus is an example of an irradiation optical system that guides the light emitted from the light source to the subject's eye. The measuring beam with which the fundus Er is irradiated is reflected and scattered by each retinal layer, returns to the fiber coupler 106 via the above-described optical path, and reaches a fiber coupler 126 via a fiber 125.

The drive control unit 180 controls the movement of the focus lens 114 in an optical axis direction. Further, according to the present exemplary embodiment, the focus lens 114 is shared by the OCT 100 and the SLO 140. However, it is not limited thereto, and each optical system may respectively include a focus lens. Further, the drive control unit 180 may control driving of the focus lens based on the difference between the wavelength employed by the light source 101 and the wavelength employed by a light source 141. For example, if the OCT 100 and the SLO 140 share the focus lens, the drive control unit 180 moves, when an operator switches imaging between the SLO 140 and the OCT 100, the focus lens according to the difference in the wavelengths. Further, if the OCT 100 and the SLO 140 respectively include the focus lens, the drive control unit 180 moves, when the focus lens in one of the optical systems is adjusted, the focus lens in the other optical system according to the difference in the wavelengths.

If an imaging mode for imaging the tomographic image of the anterior segment is selected, a focus position is set to a predetermined portion in the anterior segment instead of the fundus. Such focus adjustment with respect to the anterior segment may be performed by moving the position of the focus lens 114, or by inserting an optical member such as a dedicated lens in an optical path in front or in back of the focus lens 114. In such a case, a drive unit can insert or remove the optical member to or from the optical path. The drive control unit 180 thus inserts, if an anterior segment imaging mode is selected, the optical member in the optical path, and removes, if a fundus imaging mode is selected, the optical member from the optical path.

The reference beam acquired by the fiber coupler 106 is output via a fiber 119 from a collimator 120-a as a parallel beam. The output reference beam is then reflected via a dispersion compensation glass 121 by mirrors 123-a and 123-b mounted on a coherence gate stage 122, and reaches the fiber coupler 126 via a collimator 120-b and a fiber 124. The coherence gate stage 122 is controlled by the drive control unit 180 to deal with differences in an axial length of the subject's eye.

The return beam and the reference beam that have reached the fiber coupler 126 are combined into an interference beam. The interference beam then reaches a balanced receiver 129, i.e., a light detection unit, via fibers 127 and 128, and the balanced receiver 129 converts the interference signal to an electrical signal. A signal processing unit 190 analyzes the converted electrical signal. The optical system from the subject's eye to the balanced receiver 129 thus is an example of the imaging optical system configured to guide to the imaging unit the return beam from the subject's eye of the beam swept by the control unit. The light detection unit is not limited to the balanced receiver, and other detection units may be used.

Further, according to the present exemplary embodiment, the measuring beam and the reference beam interfere with each other in the fiber coupler 126. However, it is not limited thereto, and the mirror 123-a may be arranged so that the reference beam is reflected to the fiber 119, and the measuring beam and the reference beam may be caused to interfere with each other in the fiber coupler 106. In such a case, the mirror 123-b, the collimator 120-b, the fiber 124, and the fiber coupler 126 become unnecessary. It is desirable to use a circulator in such a configuration.

<Configuration of the SLO 140>

An example of the configuration of the SLO 140 will be described below.

The SLO 140 is an example of the fundus image acquisition unit configured to acquire the fundus image of the subject's eye.

The light source 141, i.e., a semiconductor laser, emits light having a central wavelength of 780 nm. The measuring beam emitted from the light source 141 (also referred to as a SLO measuring beam) is polarized via a fiber 142 by a polarizing controller 145 to a linearly-polarized beam, and is output from a collimator 143 as a parallel beam.

The output measuring beam then passes through a perforated portion of a perforated mirror 144, and reaches a dichroic mirror 154, via a lens 155, an X scanner 146, lenses 147 and 148, and a Y scanner 149. The X scanner 146 includes a galvano mirror that scans the fundus Er with the measuring beam in the horizontal direction, and the Y scanner 149 includes a galvano mirror that scans the fundus Er with the measuring beam in the vertical direction. It is not necessary to include the polarization controller 145. The X scanner 146 and the Y scanner 149 are controlled by the drive control unit 180, and are capable of scanning the fundus with the measuring beam in the desired range. The dichroic mirror 154 reflects light having wavelengths of 760 nm to 800 nm, and transmits light of other wavelengths.

The linearly-polarized measuring beam reflected by the dichroic mirror 154 passes through the dichroic mirror 111 and reaches the fundus Er via the optical path similar to that of the OCT 100.

The SLO measuring beam with which the fundus Er is irradiated is reflected and scattered by the fundus Er, and reaches the perforated mirror 144 via the above-described optical path. The beam reflected by the perforated mirror 144 is received via a lens 150 by an avalanche photodiode (APD) 152, converted into an electrical signal, and received by the signal processing unit 190.

The position of the perforated mirror 144 is conjugate with the position of the pupil in the subject's eye. The perforated mirror 144 reflects the light that has passed through a peripheral region of the pupil among the light reflected and scattered by the fundus Er irradiated with the measuring beam.

<The Anterior Segment Imaging Unit 160>

An example of the configuration of the anterior segment imaging unit 160 will be described below. The anterior segment imaging unit 160 includes lenses 162, 163, and 164, and an anterior segment camera 165.

An irradiation light source 115, including light emitting diodes (LED) 115-a and 115-b that emit irradiation light having a wavelength of, e.g., 850 nm, irradiates the anterior segment Ea. The light reflected by the anterior segment Ea reaches a dichroic mirror 161 via the focus lens 114, the lens 112, and the dichroic mirrors 111 and 154. The dichroic mirror 161 reflects light having wavelengths of, e.g., 820 nm to 900 nm, and transmits light of other wavelengths. The light reflected by the dichroic mirror 161 is then received by the anterior segment camera 165 via the lenses 162, 163, and 164.

The light received by the anterior segment camera 165 is converted into an electrical signal and is received by the signal processing unit 190.

<The Internal Fixation Lamp 170>

The internal fixation lamp 170 will be described below.

The interior fixation lamp 170 includes a display unit 171 and a lens 172. A plurality of LEDs arranged in a matrix shape is used as the display unit 171. A lighting position of the LED is changed under control performed by the drive control unit 180 according to a region to be imaged. The light emitted from the display unit 171 is guided to the subject's eye via the lens 172. The display unit 171 emits light having a wavelength of, e.g., 520 nm, and the drive control unit 180 displays a desired pattern.

<The Control Unit 200>

The control unit 200 will be described below. The control unit 200 includes the drive control unit 180, the signal processing unit 190, the control unit 191, and the display unit 192.

The drive control unit 180 controls each unit as described above.

The signal processing unit 190 generates images based on the signals output from the balanced receiver 129, the APD 152, and the anterior segment camera 165, analyzes the generated images, and generates visualization information of the analysis results. The image generation process will be described in detail below.

The control unit 191 controls the entire apparatus and displays, on a display screen in the display unit 192, the images generated by the signal processing unit 190. The display unit 192 is an example of a display unit or a display apparatus. Further, the image data generated by the signal processing unit 190 may be transmitted to the control unit 191 by wired or wireless communication.

The display unit 192 such as a liquid crystal display displays various types of information as described below under control of the control unit 191. The control unit 191 may transmit the image data to the display unit 192 by wired or wireless communication. Further, according to the present exemplary embodiment, the display unit 192 is included in the control unit 200. However, it is not limited thereto, and may be separated from the control unit 200.

Furthermore, a tablet, which is an example of a portable device, configured by integrating the control unit 191 and the display unit 192, may be used. In such a case, it is desirable to include a touch panel function in the display unit 192, so that a user can operate the touch panel to move the display position of the images, enlarge and reduce the images, and change the images to be displayed. The touch panel function may be included in the display unit 192 even in the case where the control unit 191 and the display unit 192 are not integrated. In other words, the touch panel may be used as an instruction device.

<Image Processing>

Image generation and image analysis processes performed in the signal processing unit 190 will be described below.

<Tomographic Image Generation and Fundus Image Generation Processes>

The signal processing unit 190 performs, on the interference signal output from the balanced receiver 129, typical reconfiguration processing, and thus generates a tomographic image.

More specifically, the signal processing unit 190 performs fixed pattern noise cancellation on the interference signal. The fixed pattern noise cancellation is performed, for example, by averaging a plurality of A-scan signals that has been detected and thus extracting the fixed pattern noise, and subtracting the extracted fixed pattern noise from the input interference signal.

The signal processing unit 190 then performs window function processing necessary for optimizing the depth resolution and dynamic range having a trade-off relation when performing Fourier transform in a finite interval. The signal processing unit 190 performs fast Fourier transform (FFT), and thus generates the tomographic image.

Figure 2A:
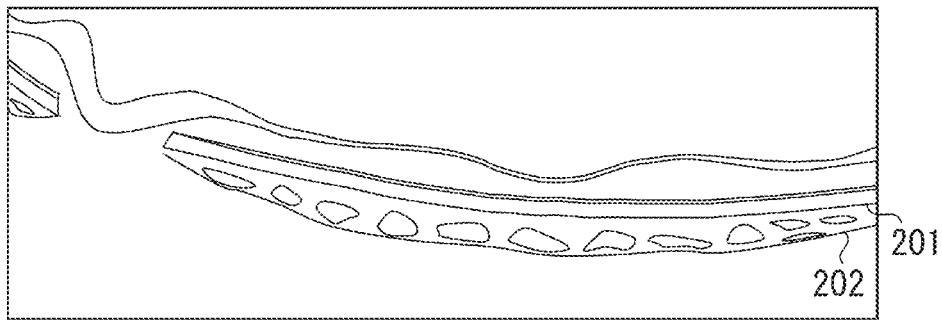
FIGS. 2A and 2B illustrate examples of the tomographic images captured by the ophthalmologic apparatus according to the first exemplary embodiment.
Figure 2B:
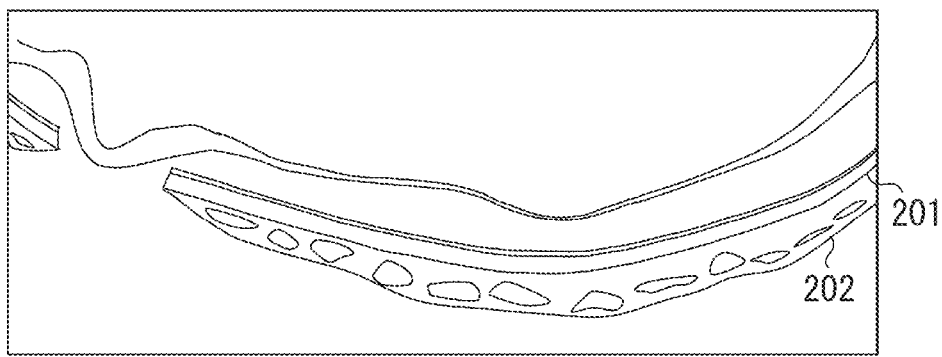

FIGS. 2A and 2B illustrate examples of the tomographic images captured by the OCT 100 and generated by the signal processing unit 190.

More specifically, FIG. 2A illustrates an example of a tomographic image of a normal eye, and FIG. 2B illustrates an example of a tomographic image of a myopic eye. Referring to FIGS. 2A and 2B, a retinal pigment epithelium-choroid boundary 201, a choroid-sclera boundary 202, and boundaries of other layers are imaged. FIGS. 2A and 2B indicate that the OCT 100 is capable of capturing the tomographic image of a wider range (i.e., wider in the horizontal direction with respect to the drawing) as compared to the SD-OCT, for the above-described reason. Further, the OCT 100 is capable of capturing the tomographic image which is deeper in the depth direction also for the reason that a wavelength of the light source used in the SS-OCT is larger than a wavelength of the light source used in the SD-OCT.

When the tomographic image is to be displayed on the display area of the display unit 192, it is meaningless to display an area in which there is no cross-sectional image. According to the present exemplary embodiment, the control unit 191 thus recognizes from data expanded in a memory in the signal processing unit 190 a portion corresponding to the cross-sectional image. The control unit 191 then cuts out from the recognized portion the tomographic image matching the size of the display area, and displays the tomographic image. The cross-sectional image indicates the image of a fundus tissue of the subject's eye.

<Segmentation>

The signal processing unit 190 performs segmentation of the tomographic image using the above-described intensity image.

More specifically, the signal processing unit 190 applies to the tomographic image to be processed, a median filter and a Sobel filter, and thus generates respective images (hereinafter referred to as a median image and a Sobel image). The signal processing unit 190 then generates a profile for each A-scan from the generated median image and Sobel image. The signal processing unit 190 generates the profile of an intensity value from the median image and the profile of a gradient from the Sobel image. The signal processing unit 190 detects peaks in the profiles generated from the Sobel image. Further, signal processing unit 190 extracts a boundary of each layer in the retina by referring to the profiles of the median image corresponding to regions before and after the detected peaks and the regions between the detected peaks.

Furthermore, the signal processing unit 190 measures each layer thickness in the direction of the A-scan line, and generates a layer thickness map of each layer.

<Processing Operation>

Figure 3:
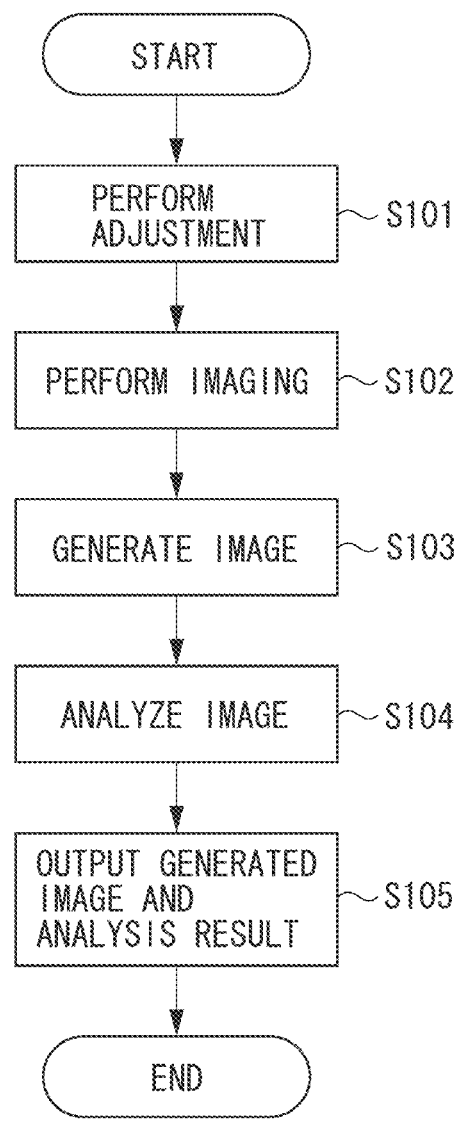
FIG. 3 is a flowchart illustrating an example of a process performed by the ophthalmologic apparatus according to the first exemplary embodiment.

The processing operation performed in the ophthalmologic apparatus according to the present exemplary embodiment will be described below. FIG. 3 is a flowchart illustrating the process performed by the ophthalmologic apparatus according to the present exemplary embodiment.

<Adjustment>

In step S101, the ophthalmologic apparatus and the subject's eye positioned on the ophthalmologic apparatus are aligned. The process unique to the present exemplary embodiment with respect to performing alignment will be described below. Since alignment of a working distance, focusing, and adjustment of the coherence gate are typical operations, description will be omitted.

<Adjustment of the OCT Imaging Position>

Figure 4:
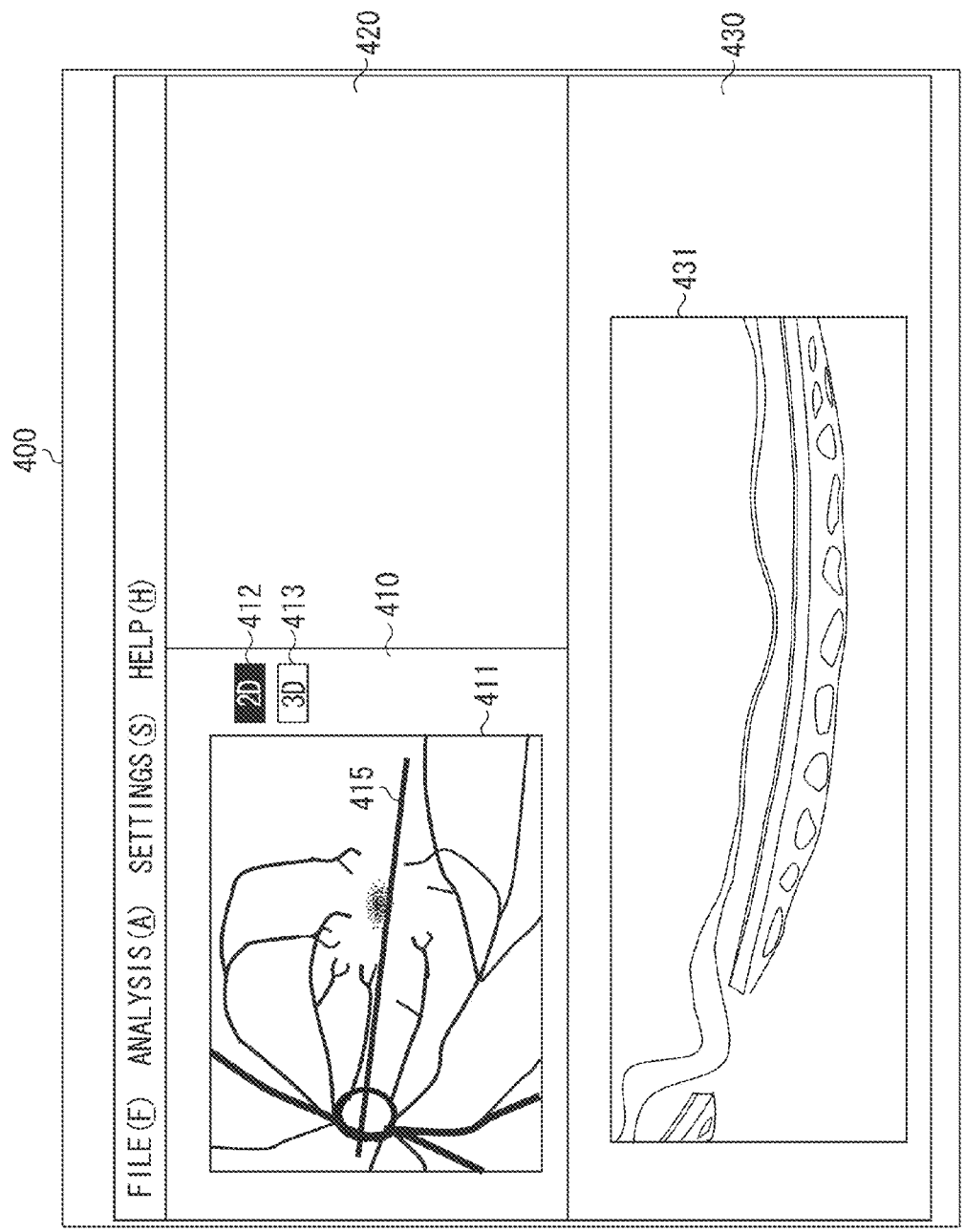
FIG. 4 illustrates a display example on a display unit according to the first exemplary embodiment.
Figure 5:
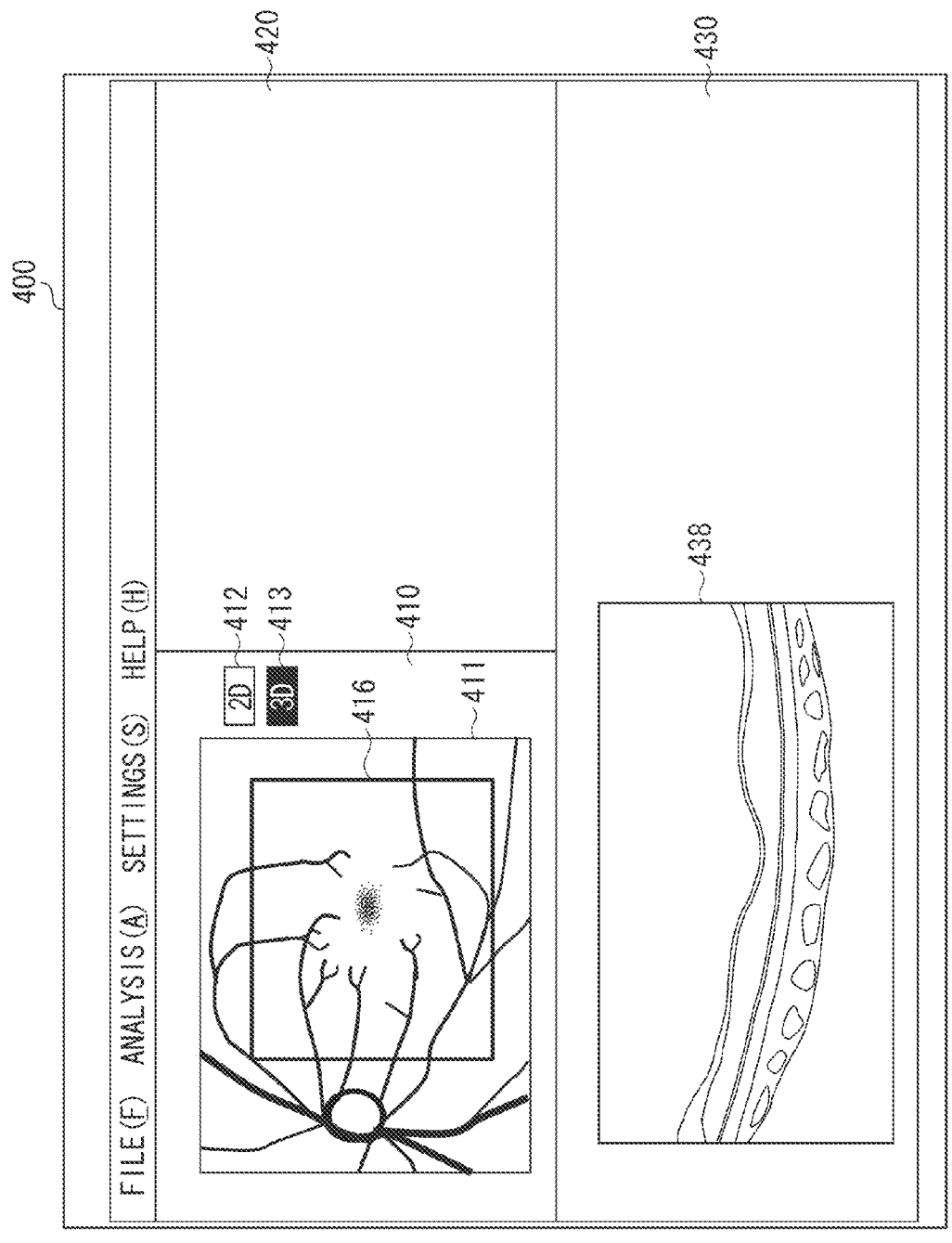
FIG. 5 illustrates a display example on the display unit according to the first exemplary embodiment.

FIGS. 4 and 5 illustrate examples of a window 400 displayed on the display unit 192 when performing adjustment or after capturing an image.

An operator using an instruction device (not illustrated) such as a mouse designates a box 412 or a box 413 by a cursor. The operator thus designates as an imaging mode, a two-dimensional (2D) imaging mode (refer to FIG. 4) or a three-dimensional (3D) imaging mode (refer to FIG. 5).

The imaging mode is then set based on the instruction and is displayed on an area 410. A fundus image (i.e., an intensity image) 411 captured by the SLO 140 and generated by the signal processing unit 190 is displayed on the area 410. The area defined by an exterior frame of the fundus image 411 is the display area of the fundus image. Hereinafter, the display area of the fundus image in the area 410 may be referred to as a fundus image display area. According to the present exemplary embodiment, the fundus image display area is an example of a first area. The fundus image 411 is a moving image captured when performing adjustment or an image captured after performing imaging.

A linear line 415 as illustrated in FIG. 4 or a rectangle 416 as illustrated in FIG. 5, indicating an imaging range of the OCT 100, is superimposed and displayed on the fundus image 411 according to the imaging mode. According to the present exemplary embodiment, a display form indicating the imaging range displayed on the fundus image 411 is not limited to the linear line and the rectangle. For example, if a circle scan is to be performed, a circle is displayed on the fundus image 411.

A tomographic image 431 illustrated in FIG. 4 is a moving image captured when performing adjustment or an image captured after performing imaging. The tomographic image 431 includes a macula lutea and an optic disk of the subject's eye. Further, a tomographic image 438 illustrated in FIG. 5 is a moving image captured when performing adjustment or an image captured after performing imaging. The areas defined by the exterior frames of the tomographic imaged 431 and 438 are the display areas of the tomographic images. Hereinafter, the display area of the tomographic image in the area 430 may be referred to as a tomographic image display area. According to the present exemplary embodiment, the tomographic image display area is an example of a second area positioned above or below the first area and which is an area wider in the horizontal direction as compared to the first area.

The tomographic image display area may also be an area larger in the vertical direction (i.e., in the vertical direction with respect to the display unit 192) as compared to the fundus image display area. In other words, the second area may be larger in the vertical direction as compared to the first area.

As illustrated in FIGS. 4 and 5, the size of the tomographic image display area may be changed according to the imaging range of the tomographic image. More specifically, if the viewing angle of the tomographic image is greater than or equal to a predetermined value, the horizontal width of the tomographic image display area may be increased as illustrated in FIG. 4. Further, if the imaging range of the tomographic image is a viewing angle that is less than a predetermined value, the horizontal width of the tomographic image display area may be decreased as illustrated in FIG. 5.

The operator designates the imaging range using the instruction device (not illustrated) such as the mouse. In other words, the operator sets the size and adjusts the position of the linear line 415 and the rectangle 416 using the instruction device. The drive control unit 180 then controls a drive angle of a scanner and determines the imaging range. For example, if the operator has selected the 2D imaging mode, the imaging range may be instructed by automatically extracting the macula lutea and the optic disk from the fundus image 411, and setting a linear line that passes through the macula lutea and the optic disk as an initial tomographic image acquisition position. Further, the operator may use the instruction device to designate two points on the fundus image 411, so that a linear line connecting the two points is set as the tomographic image acquisition position.

The example illustrated in FIG. 4 is a case where one tomographic image is captured. In contrast, according to the example illustrated in FIG. 5, a three-dimensional image is captured, and a tomographic image 432 near the center of the area is displayed in the area 430. The tomographic image 438 is not limited to the tomographic image near the center of the rectangle 416, and may be the tomographic image of an edge portion of the rectangle 416. An examiner may also preset the position in the rectangle 416 which is to be displayed as the tomographic image.

<Imaging, Image Generation, and Analysis>

In step S102, the light sources 101 and 141 respectively emit the measuring beam based on an imaging instruction from the operator. The control unit 191 sweeps the wavelength of the light emitted from the light source 101. The balanced receiver 129 and the APD 152 then receive the return beam from the fundus Er. In step S103 and step S104, the signal processing unit 190 generates and analyzes each image as described above.

<Output>

The process for outputting the generated image and the analysis result performed in step S105 will be described below.

After the signal processing unit 190 completes generating and analyzing of each image, the control unit 191 generates output information based on the result, and outputs to and displays on the display unit 192 the information. The display examples on the display unit 192 will be described below.

<The Display Screen>

FIGS. 4, 5, 6, 7, 8, and 9 illustrate display examples on the display unit 192 according to the present exemplary embodiment.

Referring to FIG. 4, the window 400 includes the area 410, an area 420, and the area 430. More specifically, the areas 410 and 420 are arranged adjacent to each other above the area 430. The display example is not limited thereto, and the areas 410 and 420 may be arranged adjacent to each other below the area 430. Further, in the example illustrated in FIG. 4, the area 410 is positioned to the left of the area 420. However, it is not limited thereto, and the area 420 may be arranged to the left of the area 410. Furthermore, in the example illustrated in FIG. 4, the window 400 includes three areas. However, it is not limited thereto, and the area may include four or more areas, or two or less areas.

The area 430 displays the tomographic image 431, and the area 410 displays the fundus image 411. In other words, the fundus image display area is positioned above or below the tomographic image display area.

The area 420 displays information on the apparatus and information on a subject. As illustrated in FIG. 4, the horizontal width of the area 430 is wider than those of the areas 410 and 420. Further, the horizontal width of the tomographic image 431 is wider than that of the fundus image 411. The width of the tomographic image display area is thus wider than that of the fundus image display area. Furthermore, the sum of the horizontal widths of the areas 410 and 420 is equal to the horizontal width of the area 430. However, it is not limited thereto. The control unit 191 displays on the display unit 192 the tomographic image 431 and the fundus image 411. The control unit 191 thus is an example of the display control unit configured to display the fundus image in the first area of the display unit, and the tomographic image in the second area of the display unit which is positioned above or below the first area and which is an area wider in the horizontal direction as compared to the first area.

Moreover, as illustrated in FIG. 4, the tomographic image 431 is displayed in the tomographic image display area set in the area 430 having a wider horizontal width as compared to the areas 410 and 420. As a result, the tomographic image 431 can be displayed wider in the horizontal direction as compared to the images displayed in the other areas. The tomographic image 431 can thus be displayed without reducing the tomographic image of a wide imaging angle, or be displayed by reducing a reduction ratio. In other words, a tomographic image of a wide viewing angle can be easily observed.

According to the present exemplary embodiment, since the OCT 100 has a deep imaging area, a tomographic image of a predetermined depth (i.e. a length in the vertical direction with respect to the drawing) from the coherence gate position is cut out and displayed to match the tomographic image display area.

Figure 7:
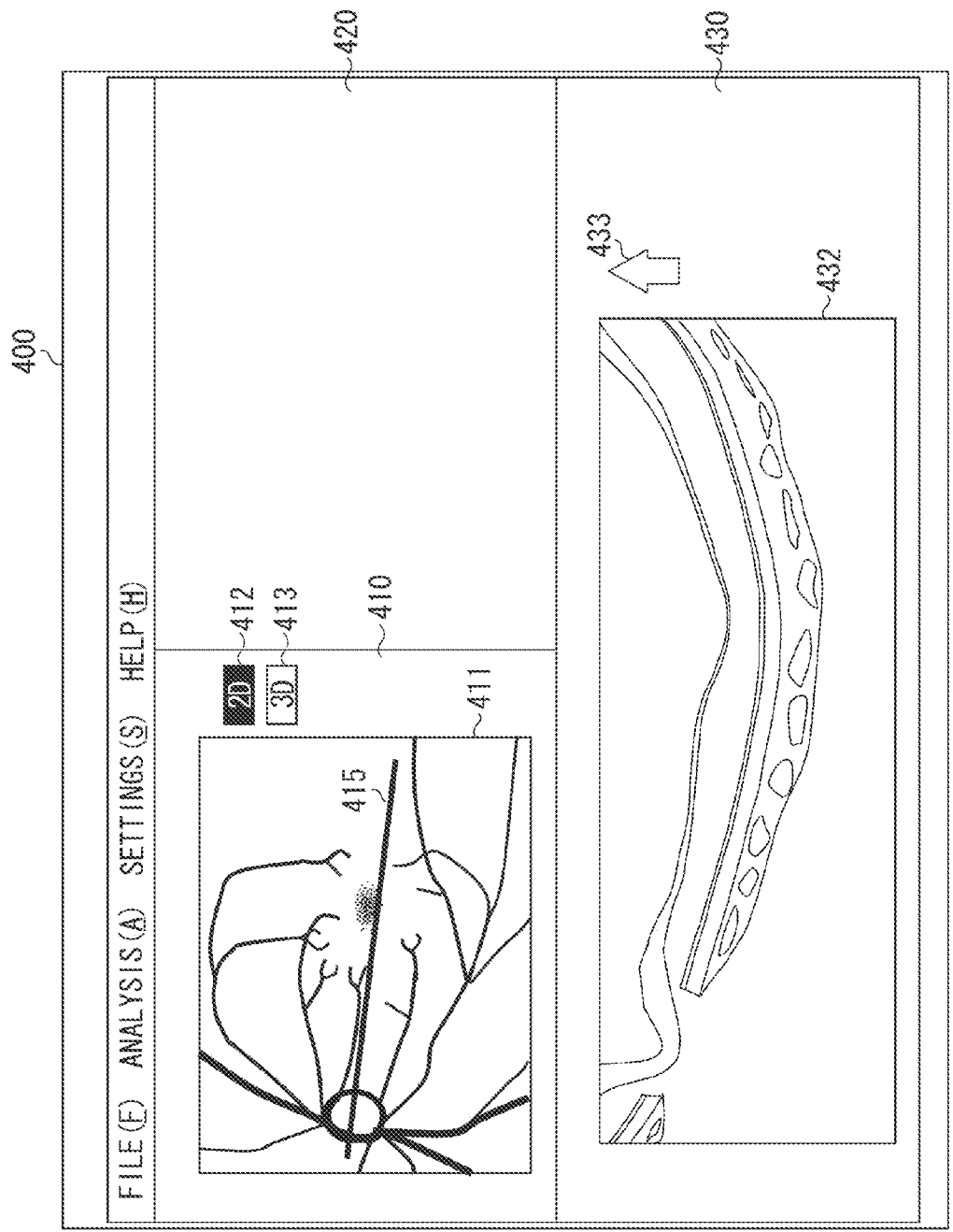
FIG. 7 illustrates a display example on the display unit according to the first exemplary embodiment.
Figure 8:
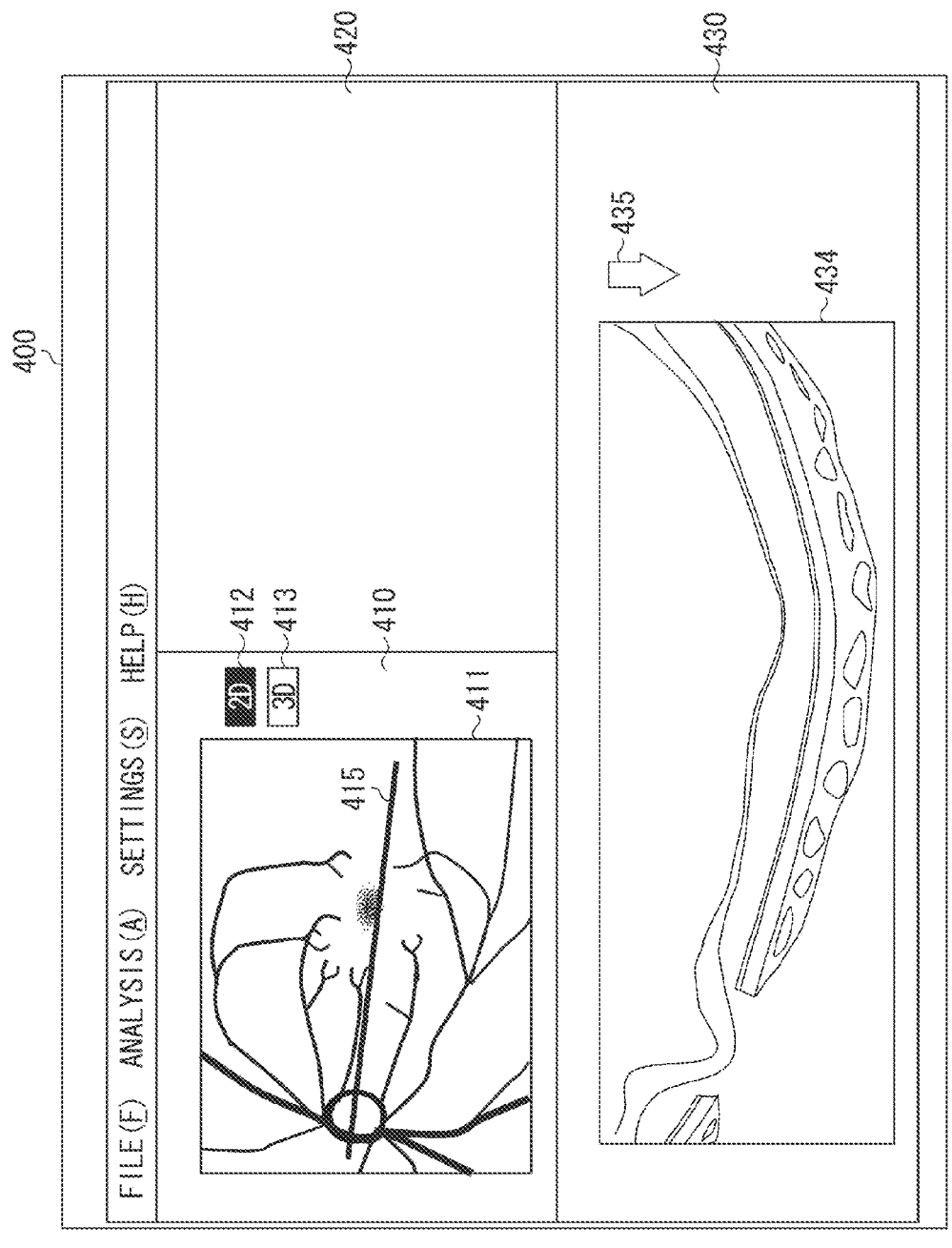
FIG. 8 illustrates a display example on the display unit according to the first exemplary embodiment.

If it is determined that, as a result of cutting out the tomographic image, the cross-sectional image in the tomographic image intersects a line defining the vertical direction of the tomographic image display area, the control unit 191 displays a designation area 433 as illustrated in FIG. 7. Referring to FIG. 7, if the operator designates the designation area 433 by clicking thereon, the control unit 191 may expand the tomographic image display area as illustrated in FIG. 8, and more display the entire tomographic image. As a result, a tomographic image 434 as illustrated in FIG. 8 which is larger than the tomographic image 432 in the depth direction is displayed. In other words, if it is determined that the cross-sectional image and the line defining the vertical direction of the tomographic image display area intersect, the control unit 191 expands the area 430.

Referring to FIG. 8, if the use designates a designation area 435, the display returns to the state illustrated in FIG. 7. Further, in the example illustrated in FIG. 8, the fundus image 411 is superimposed on the area 430 and displayed. However, the fundus image 411 may be reduced and displayed, such that the fundus image 411 and the area 430 do not overlap. The fundus image display area may thus be reduced.

If the operator designates the designation area 433, the tomographic image display area may be expanded over the entire window 400 to display on the display unit 192 the portions of the tomographic image 432 that has not been displayed. Further, if the operator has selected a portion of the tomographic image displayed on the entire window 400, the control unit 191 may cut out the tomographic image including the selected portion and return to the display state illustrated in FIG. 7. The control unit 191 thus displays the tomographic image including the selected portion as the tomographic image 432 as illustrated in FIG. 7. As a result, the examiner can easily display the tomographic image of the desired position. According to the above-described examples, the display form is changed by designating the designation areas 433 and

435. However, it is not limited thereto, and the display form may be changed according to the operator double-clicking on the tomographic image 432.

Further, when the control unit 191 determines that the cross-sectional image and the line defining the vertical direction of the tomographic image display area intersect, it is not necessary for the control unit 191 to display the designation area 433. In such a case, the control unit 191 may automatically expand the tomographic image display area so that the tomographic image 432 becomes the tomographic image 434. In other words, if the image of the fundus tissue of the subject's eye included in the tomographic image contacts an upper edge of the second area, the control unit 191 expands the second area, and displays the tomographic image on the expanded second area. Further, in such a case, the control unit 191 reduces the fundus image 411 so that the fundus image 411 and the area 430 do not overlap. In other words, if the second area is expanded, the first area and the fundus image are reduced, so that the designation areas 433 and 435 become unnecessary.

Figure 9A:
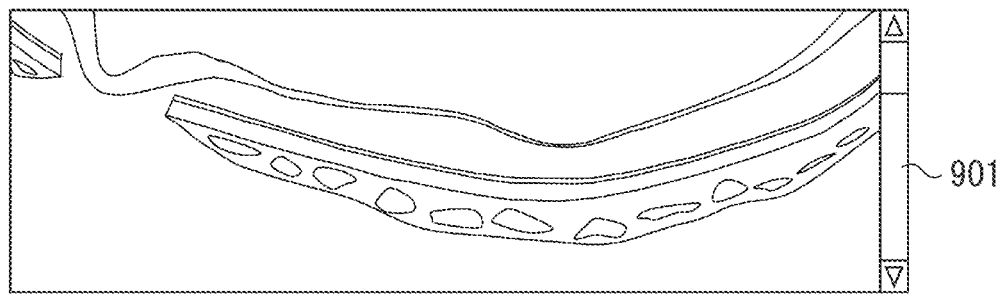
FIGS. 9A and 9B illustrates display examples on the display unit according to the present exemplary embodiment.
Figure 9B:
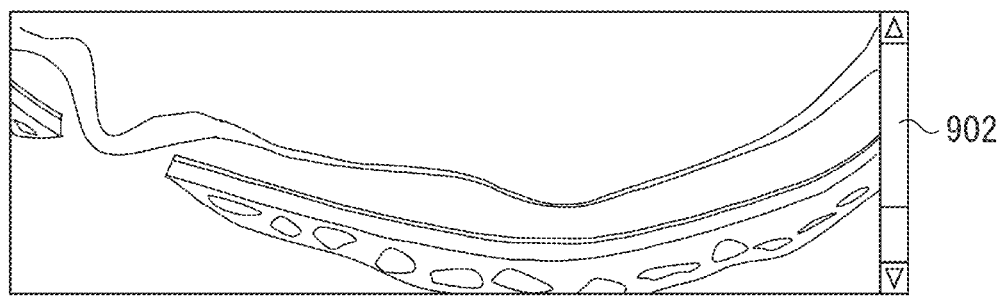

Furthermore, as illustrated in FIGS. 9A and 9B, areas 901 and 902 for scrolling the tomographic image may be added to the tomographic image, and the operator may scroll the tomographic image by giving an instruction thereon, instead of enlarging the area as described above. FIG. 9B illustrates the display example in the case where the operator scrolls upward from the state illustrated in FIG. 9A. The control unit 191 adds the areas 901 and 902. The control unit 191 may add the areas 901 and 902 only when it is determined that the cross-sectional image and the line defining the vertical direction of the tomographic image display area intersect, or may regularly add the areas 901 and 902. The display control unit thus displays, if the image of the fundus tissue of the subject's eye included in the tomographic image contacts the upper edge of the second area, the scroll bar which scrolls the tomographic image displayed on the display unit in the vertical direction.

FIG. 5 illustrates the state where the tomographic image 438 is displayed on the area 430 as the tomographic image captured in the 3D imaging mode. The OCT 100 acquires as the three-dimensional data the information of the area set by the rectangle 416, and the control unit 191 displays on the display unit 192 the tomographic image 438 near the center of the rectangle 416. The tomographic image 438 is not limited to the tomographic image near the center of the rectangle 416, and may be the tomographic image of the edge portion of the rectangle 416.

Figure 6:
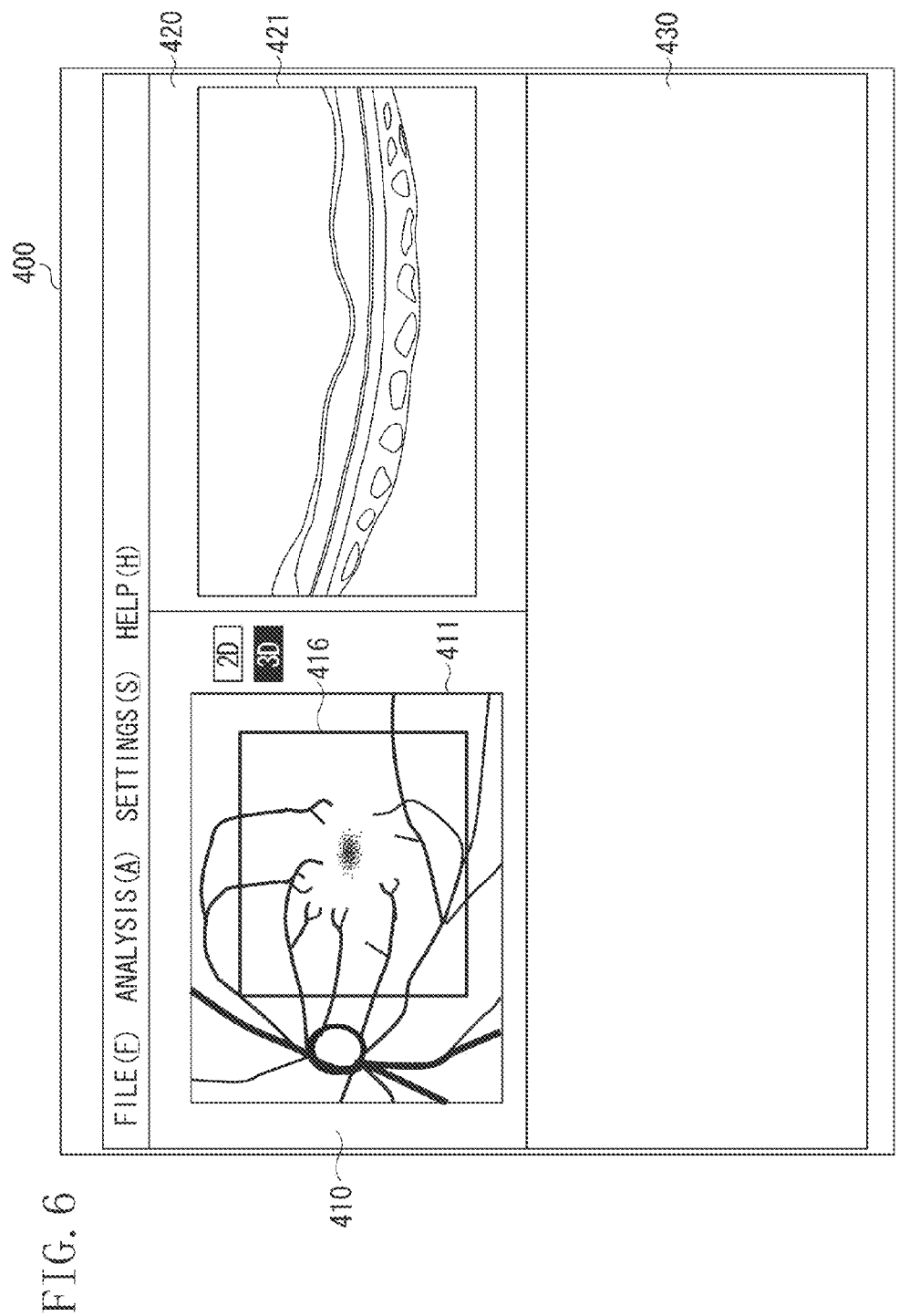
FIG. 6 illustrates a display example on the display unit according to the first exemplary embodiment.

A display screen as illustrated in FIG. 6 may be displayed instead of the display screen illustrated in FIG. 5. Referring to FIG. 6, the area defined by the exterior frame of a tomographic image 421 is positioned to the right of the fundus image display area. However, it is not limited thereto, and the area may be positioned to the left of the fundus image display area. Further, the area defined by the exterior frame of a tomographic image 421 is positioned above the tomographic image display area. However, it is not limited thereto, and the area may be positioned below the tomographic image display area. Furthermore, the area defined by the exterior frame of a tomographic image 421 is narrower in the horizontal direction as compared to the tomographic image display area. In other words, the area defined by the exterior frame of a tomographic image 421 is an example of a third area which is positioned to the left or the right of the first area and which is an area narrower in the horizontal direction as compared to the second area. In such a case, the display area of the tomographic image becomes smaller, so that the information on the apparatus can be displayed on a wide area. The display areas can thus be efficiently used in the display states illustrated in FIGS. 4 and 6.

The control unit 191 may switch between display as illustrated in FIG. 4 and display as illustrated in FIG. 6 according to the imaging range. For example, if the viewing angle of the imaging range is wider than the predetermined value, the control unit 191 may perform display as illustrated in FIG. 4, and if the imaging range is less than or equal to the predetermined value, the control unit 191 may perform display as illustrated in FIG. 6. The display control unit thus determines the area for displaying the tomographic image according to the viewing angle of the tomographic image. More specifically, the display control unit displays the tomographic image whose viewing angle is greater than or equal to a threshold value on the first area. Further, the display control unit displays the tomographic image whose viewing angle is less than the threshold value on the third area which is positioned to the left or the right of the first area and which is an area narrower in the horizontal direction as compared to the second area.

According to the above-described example, the control unit 191 switches the display form according to the viewing angle. However, the area for displaying the tomographic image may be changed based on whether the tomographic image includes both or one of the optic disk and the macula lutea. For example, if the tomographic image includes both of the optic disk and the macula lutea, the control unit 191 displays the tomographic image as illustrated in FIG. 4. If the tomographic image only includes the optic disk or the macula lutea, the control unit 191 displays the tomographic image as illustrated in FIG. 6. The display control unit thus displays, if the tomographic image includes both the optic disk and the macula lutea of the subject's eye, the tomographic image on the first area. Further, the display control unit displays, if the tomographic image only includes the optic disk or the macula lutea, the tomographic image on the third area which is positioned to the left or the right of the first area and which is an area narrower in the horizontal direction as compared to the second area.

As a result, the area to be displayed is determined according to the viewing angle or a characteristic portion such as the optic disk and the macula lutea. The area of the display screen can thus be efficiently used.

As described above, according to the present exemplary embodiment, the tomographic image of a wide viewing angle captured using the SS-OCT can be efficiently displayed. Further, if the tomographic image cannot be fully displayed in a preset tomographic image display area, the tomographic image is displayed by enlarging the area. The tomographic image can thus be displayed without lowering the resolution or by suppressing lowering of the resolution. Furthermore, if the tomographic image cannot be fully displayed in the preset tomographic image display area, the tomographic image is displayed by scrolling the area. The tomographic image of the portion to be observed can thus be displayed.

MODIFIED EXAMPLE

Figure 10:
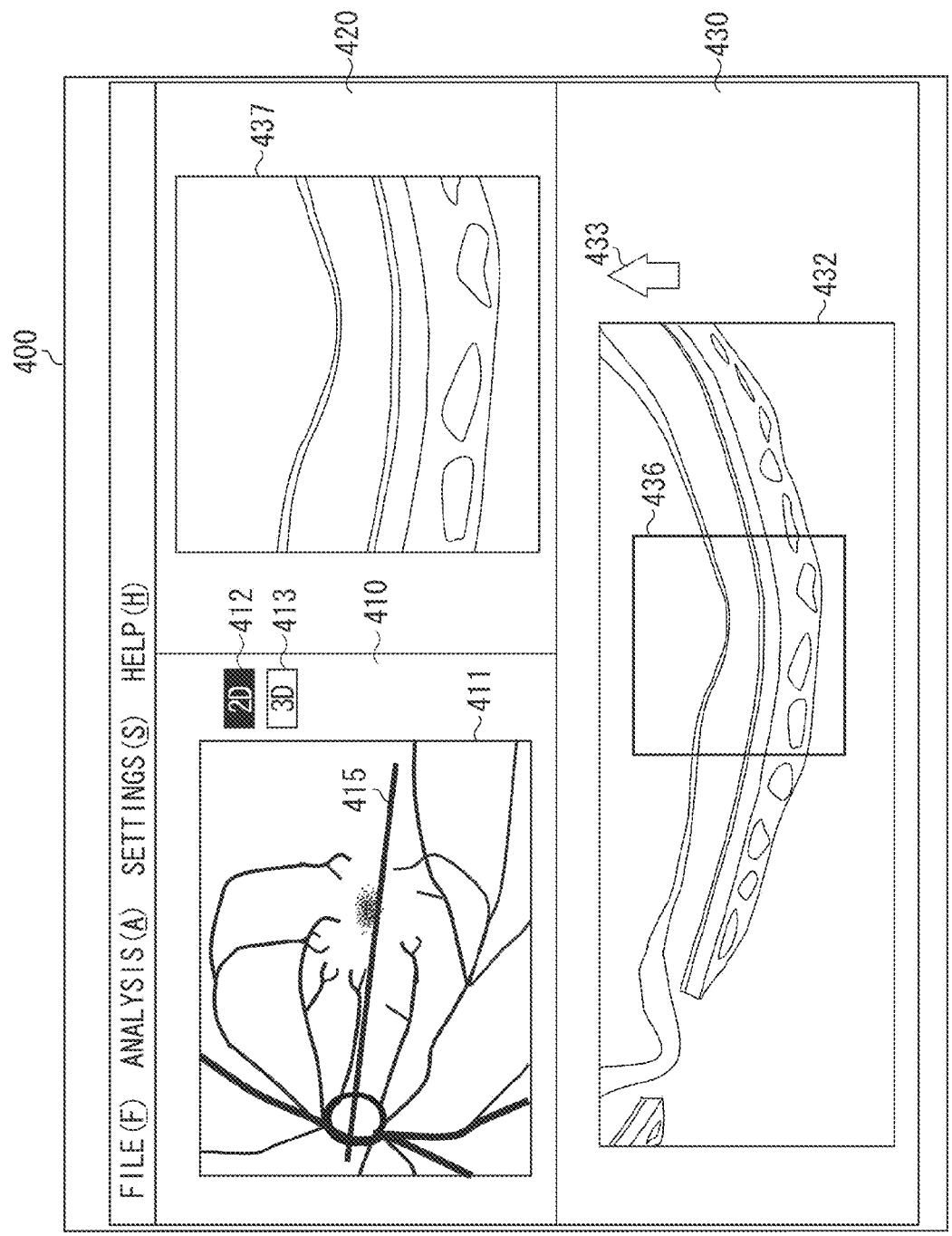
FIG. 10 illustrates a display example on the display unit according to the first exemplary embodiment.

The display example on the display unit 192 is not limited to the above. For example, the display unit 192 may display the tomographic image as illustrated in FIG. 10. Referring to FIG. 10, the area 430 displays the tomographic image 432 captured by the OCT 100. If the operator then selects using the instruction device such as the mouse a portion of the tomographic image 432 displayed on the area 430, the control unit 191 displays on the area 420 a tomographic image 437 of a selected area 436. The area defined by the exterior frame of the tomographic image 437 is an example of the third area. Since the area defined by the exterior frame of the tomographic image 437 is proximately similar to the above-described area defined by the exterior frame of the tomographic image 421, detailed description on the positional relation with the other areas will be omitted.

The control unit 191 enlarges the tomographic image in the area 436 to match the size of the area 420 and displays the tomographic image. The display control unit thus enlarges, if a selection unit selects a portion of the tomographic image displayed on the second area, the selected portion of the tomographic image. The display control unit displays the enlarged tomographic image on the third area which is positioned to the left or the right of the first area and which is an area narrower in the horizontal direction as compared to the second area. The control unit 191 displays on the tomographic image 432 the area 436 selected using the instruction device.

According to the above-described modified example, a positional relation between the tomographic image of a wide viewing angle and a portion of the tomographic image becomes recognizable. Further, a portion of the tomographic image of a wide viewing angle can be observed in detail. As a result, an efficient diagnosis can be performed.

According to the first exemplary embodiment, the SS-OCT and the SLO are integrated in the apparatus. According to the second exemplary embodiment, the fundus camera is used instead of the SLO as the optical system for observing the fundus of the subject's eye, and the SS-OCT and the fundus camera are integrated in the apparatus.

Further, according to the first exemplary embodiment, the X scanner 107 and the Y scanner 110 are separately included in the OCT 100. In contrast, according to the present exemplary embodiment, the scanners are integrally configured as an XY scanner 338, and included in a fundus camera main body 300. However, the present invention is not limited thereto.

Furthermore, according to the present exemplary embodiment, an infrared area sensor 321 for performing infrared fundus observation is included in the fundus camera main body 300 separately from a camera unit 330. If an area sensor 331 in the camera unit 330 is sensitive to both the infrared light and the visible light, it is not necessary to include the infrared area sensor 321.

Figure 11:
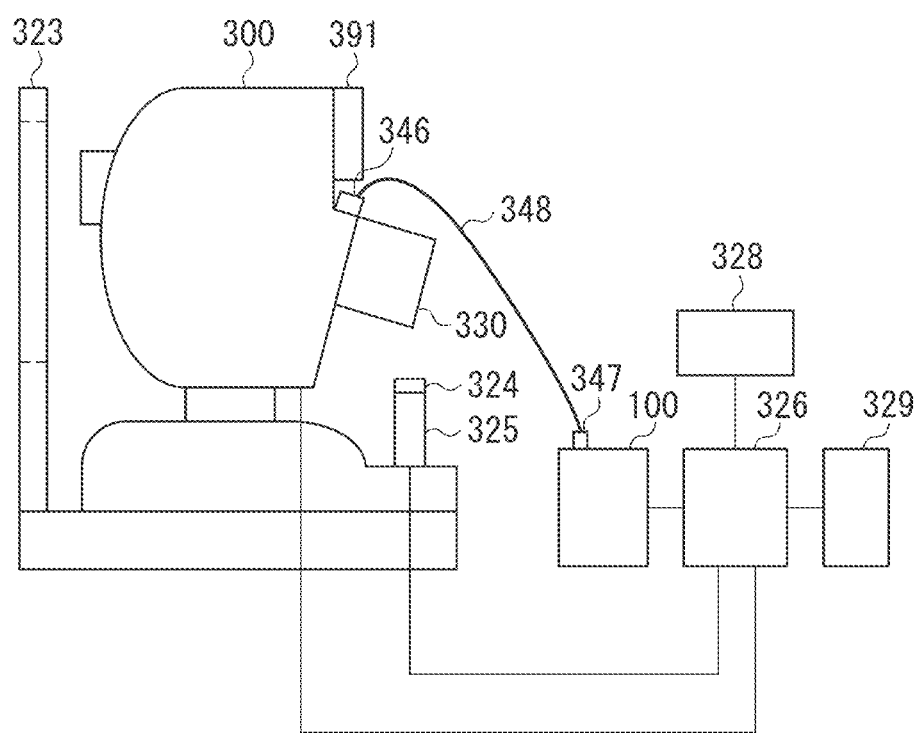
FIG. 11 is a lateral view illustrating an imaging apparatus according to a second exemplary embodiment of the present invention.

The entire configuration of the imaging apparatus according to the present exemplary embodiment will be described below with reference to FIG. 11. FIG. 11 is a lateral view illustrating the imaging apparatus according to the present exemplary embodiment. Referring to FIG. 11, the fundus camera main body 300 and the camera unit 330 are optically connected. Further, the fundus camera main body 300 and the OCT 100 are optically connected via an optical fiber 348. Furthermore, the fundus camera main body 300 and the OCT 100 respectively include a connector 346 and a connector 347. A chin support 323 fixes a chin and a forehead of the subject so that the subject's eye is fixed to capture an image. A monitor 391 displays an infrared image for performing adjustment in imaging.

A joystick 325 is used by the examiner for controlling movement of the fundus camera main body 300 to align with the subject's eye. An operation switch 324 is a signal input unit used for inputting the operations for capturing the tomographic image and the fundus image. A control unit 326 which is a personal computer controls the fundus camera main body 300, the camera unit 330, and display of the configuration of the tomographic image, the tomographic image and the fundus image. A control unit monitor 328 is a display unit, and a storing unit 329 is a hard disk that stores programs and captured images. The storing unit 329 may be included in the control unit 326. The camera unit 330 is a general-purpose digital single-lens reflex camera, and is connected to the fundus camera main body 300 by a general-purpose camera mount.

<The Optical System of the Fundus Camera Main Body>

Figure 12:
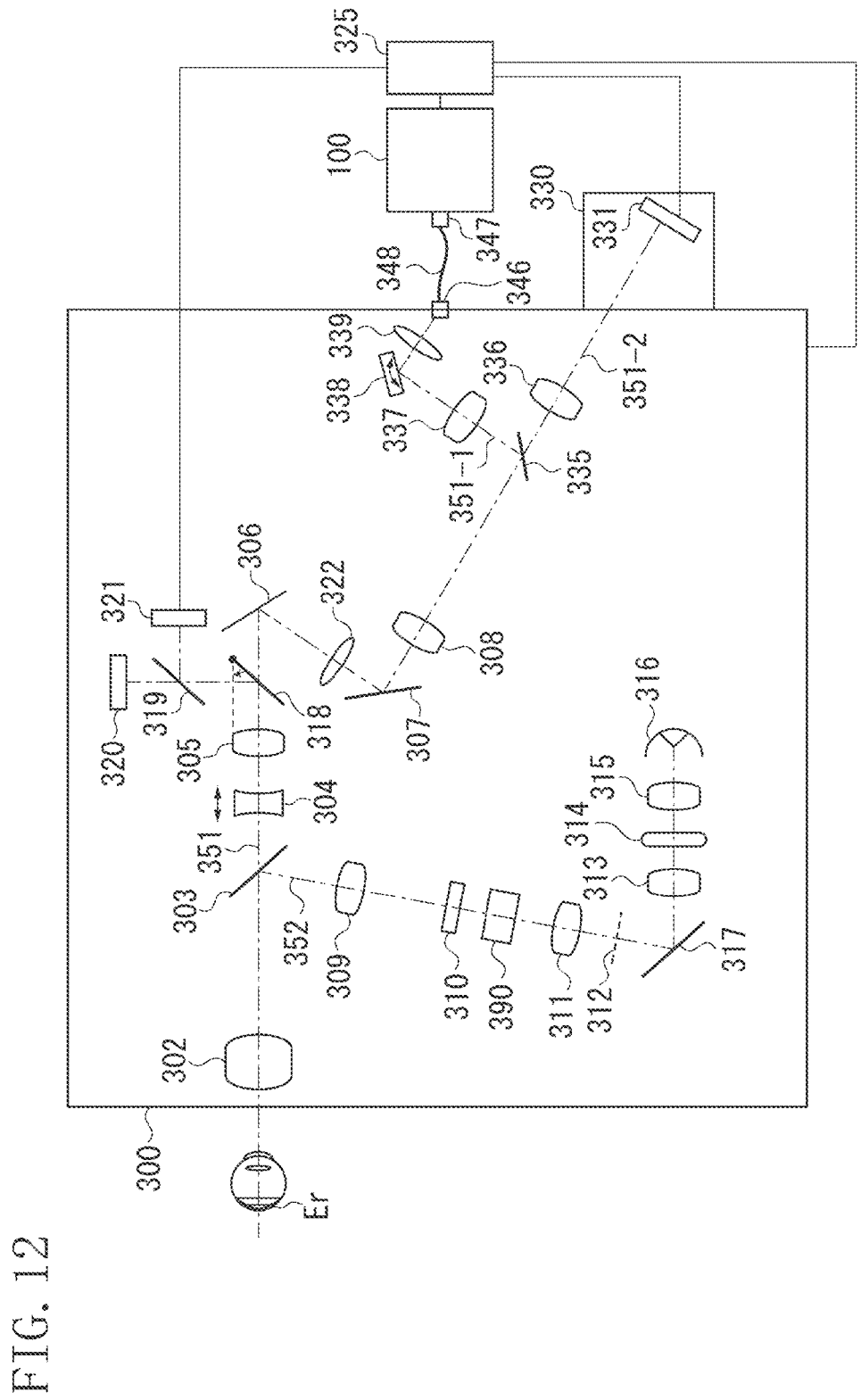
FIG. 12 is a schematic diagram illustrating an example of an optical system in a fundus camera main body according to the second exemplary embodiment.

The optical system of the fundus camera main body 300 will be described below with reference to FIG. 12. FIG. 12 is a schematic diagram illustrating the optical system of the fundus camera main body 300.

Referring to FIG. 12, an objective lens 302 is disposed opposing the subject's eye, and a perforated mirror 303 on the optical axis divides the optical path into an optical path 351 and an optical path 352. The optical path 352 forms an irradiation optical system that irradiates the fundus Er of the subject's eye. A halogen lamp 316 used for performing alignment of the subject's eye and a stroboscopic tube 314 used for imaging the fundus Er of the subject's eye are arranged in a lower portion of the fundus camera main body 300. Further, the fundus camera main body 300 includes condenser lenses 313 and 315 and a mirror 317.

The illuminating light from the halogen lamp 316 and the stroboscopic tube 314 is formed into a ring-shaped light bundle by a ring slit 312, reflected by the perforated mirror 303, and irradiates the fundus Er of the subject's eye. The light emitted from the halogen lamp 316 irradiates the subject's eye as light of the wavelength range of, e.g., 700 nm to 800 nm. The light of the wavelength range of, e.g., 400 nm to 700 nm is emitted from the stroboscopic tube 314, with which the subject's eye is irradiated.

Furthermore, the fundus camera main body 300 includes lenses 309 and 311, and an optical filter 310. An alignment optical system 390 projects a split image for focusing on the fundus Er, or an index for matching the subject's eye with the optical axis of the optical path of the optical system in the fundus camera main body 300.

The optical path 351 forms an imaging optical system for capturing the tomographic image and the fundus image of the fundus Er of the subject's eye. A focus lens 304 and an image forming lens 305 are arranged on the right side of the perforated mirror 303. The focus lens 304 is supported to be movable in the optical axis direction by the examiner operating a knob (not illustrated).

The optical path 351 is guided via a quick return mirror 318 to a fixation lamp 320 and the infrared area sensor 321. The quick return mirror 318 reflects the infrared light for capturing the fundus observation image (e.g., light of 700 nm to 800 nm wavelength range), and transmits the infrared light of the wavelength range used in capturing the tomographic image (e.g., light of 980 nm to 1100 nm wavelength range). Further, a silver film and a protection film thereof are formed in this order on the surface of the quick return mirror 318. If the infrared area sensor 321 is to capture the moving image and the tomographic image of the fundus using the infrared light, the quick return mirror 318 is inserted in the optical path. It is desirable that the quick return mirror 318 does not transmit visible light (e.g., light of 400 nm to 700 nm wavelength range) that is unnecessary in capturing the moving image and the tomographic image of the fundus. On the other hand, if the still image of the fundus is to be captured using the visible light, a control unit (not illustrated) removes the quick return mirror 318 from the optical path 351.

The image information acquired by the infrared area sensor 321 is displayed on the display unit 328 or the monitor 391, and used for performing alignment of the subject's eye. Further, a dichroic mirror 319 is configured such that the visible light is guided towards the fixation lamp 320 and the infrared light is guided towards the infrared area sensor 321. The optical path 351 is then guided to the camera unit 330 via a mirror 306, a field lens 322, a mirror 307, and a relay lens 308. The quick return mirror 318 may be a dichroic mirror which reflects light of, e.g., 700 nm to 800 nm wavelength range and transmits light of, e.g., 980 nm to 1100 nm wavelength range.

The optical path 351 is then divided via a dichroic mirror 335 into a tomographic imaging optical path 351-1 and a visible fundus imaging optical path 351-2. The dichroic mirror 335 transmits light of, e.g., 400 nm to 700 nm wavelength range and reflects light of, e.g., 980 nm to 1100 nm wavelength range. According to the present exemplary embodiment, the tomographic imaging optical path 351-1 and the visible fundus imaging optical path 351-2 are respectively configured as the reflected light path and the transmitted light path. However, the configuration may be reversed. In such a case, the wavelength range of the light transmitted by the dichroic mirror 335 and the wavelength range of the light reflected by the dichroic mirror 335 are reversed. Further, since light of the wavelength range between the light used in tomographic imaging and the light used in visible fundus imaging is unnecessary, the dichroic mirror 335 may be configured not to transmit or reflect (e.g., absorb) such a wavelength range. An optical member that cuts such a wavelength range may instead be disposed in a stage previous to the dichroic mirror 335.

The fundus camera main body 300 also includes relay lenses 336 and 337, the XY scanner 338, and a collimate lens 339. The XY scanner 338 is illustrated as a single mirror for ease of description. However, two mirrors, i.e., the X scan mirror and the Y scan mirror, are actually arranged close to each other, and perform raster scanning on the fundus Er in the direction perpendicular to the optical axis. Further, the optical axis of the tomographic imaging optical path 351-1 is adjusted to match the rotational centers of the two mirrors of the XY scanner 338. Furthermore, the connector 346 is used for attaching the optical fiber.

The camera unit 330 is a digital single-reflex camera for imaging the fundus Er. The fundus camera main body 300 and the camera unit 330 are connected via a general-purpose camera mount, so that the fundus camera main body 300 and the camera unit 330 can be easily attached to and separated from each other. The fundus image is formed on the surface of the image area sensor 331.

The present exemplary embodiment is capable of acquiring a similar effect as the first exemplary embodiment.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2012-082687 filed Mar. 30, 2012, which is hereby incorporated by reference herein in its entirety.

What is claimed is:

1. An ophthalmologic apparatus comprising:
an irradiation optical system configured to guide light emitted from a light source to the subject's eye;
a control unit configured to sweep a wavelength of light emitted from the light source;
an imaging optical system configured to guide to an imaging unit a return beam from the subject's eye of light swept by the control unit;
a tomographic image acquisition unit configured to acquire a tomographic image of the subject's eye based on an output from the imaging unit;
a fundus image acquisition unit configured to acquire a fundus image of the subject's eye; and
a display control unit configured to display the fundus image on a first area in a display unit and display the tomographic image on a second area in the display unit which is positioned above or below the first area and is wider in a horizontal direction as compared to the first area, wherein the display control unit changes a size of the second area in accordance with a viewing angle of the tomographic image.

2. The ophthalmologic apparatus according to claim 1, wherein the second area is an area larger in a vertical direction as compared to the first area.

3. The ophthalmologic apparatus according to claim 1, wherein the tomographic image includes a macula lutea and an optic disk of the subject's eye.

4. The ophthalmologic apparatus according to claim 1, wherein the display control unit expands, in the case where an image of a fundus tissue of the subject's eye included in the tomographic image contacts an upper edge of the second area, the second area, and displays the tomographic image on the expanded second area.

5. The ophthalmologic apparatus according to claim 4, wherein, in the case where the second area is expanded, the first area and the fundus image are reduced.

6. The ophthalmologic apparatus according to claim 1, wherein the display control unit displays, in the case where an image of a fundus tissue of the subject's eye included in the tomographic image contacts an upper edge of the second area, a scroll bar that scrolls the tomographic image displayed on the display unit in a vertical direction.

7. The ophthalmologic apparatus according to claim 1, wherein the display control unit determines an area in which the tomographic image is to be displayed according to a viewing angle of the tomographic image.

8. The ophthalmologic apparatus according to claim 7, wherein the display control unit displays on the second area a tomographic image of the viewing angle that is greater than or equal to a threshold value, and displays on a third area of the display unit, which is positioned to the left or the right of the first area and is narrower in a horizontal direction as compared to the second area, a tomographic image of the viewing angle that is less than the threshold value.

9. The ophthalmologic apparatus according to claim 1, wherein the display control unit displays, in the case where the tomographic image includes a macula lutea and an optic disk of the subject's eye, the tomographic image in the second area, and displays, in the case where the tomographic image only includes one of the macula lutea and the optic disk, the tomographic image on a third area of the display unit, which is positioned to the left or the right of the first area and is narrower in a horizontal direction as compared to the second area.

10. The ophthalmologic apparatus according to claim 1, wherein the display control unit enlarges, in the case where a portion of a tomographic image displayed on the second area is selected using a selection unit, the selected portion of the tomographic image, and displays the enlarged portion on a third area of the display unit, which is positioned to the left or the right of the first area and is narrower in a horizontal direction as compared to the second area.

11. The ophthalmologic apparatus according to claim 1, wherein the display control unit displays a scroll bar that scrolls the tomographic image displayed on the display unit in a vertical direction.

12. The ophthalmologic apparatus according to claim 1, wherein the display control unit changes the horizontal width of the second area in accordance with a viewing angle the of the tomographic image.

13. The ophthalmologic apparatus according to claim 12, wherein the display control unit reduces the horizontal width of the second area in a case where the viewing angle of the tomographic image is less than a predetermined value.

14. A method of displaying information from an ophthalmologic apparatus, the ophthalmologic apparatus comprising: an irradiation optical system that guides light emitted from the light source to a subject's eye; sweeping a wavelength of light emitted from the light source; guiding a return beam of the swept light from the subject's eye; acquiring a tomographic image of the subject's eye based on the return beam; acquiring a fundus image of the subject's eye; comprising:
displaying the fundus image on a first display area; and
displaying the tomographic image on a second area;
wherein the second area is positioned above or below the first area and is wider in a horizontal direction as compared to the first display area, wherein a size of the second area is changed in accordance with a viewing angle of the tomographic image.

15. A non-transitory computer readable medium encoded with instructions for displaying information from an ophthalmologic apparatus, the ophthalmologic apparatus comprising: an irradiation optical system that guides light emitted from the light source to a subject's eye; sweeping a wavelength of light emitted from the light source; guiding a return beam of the swept light from the subject's eye; acquiring a tomographic image of the subject's eye based on the return beam; acquiring a fundus image of the subject's eye; comprising:
instructions for displaying the fundus image on a first display area; and
instructions for displaying the tomographic image on a second area;
wherein the second area is positioned above or below the first area and is wider in a horizontal direction as compared to the first display area, wherein a size of the second area is changed in accordance with a viewing angle of the tomographic image.

16. An ophthalmologic apparatus comprising:
an irradiation optical system configured to guide light emitted from a light source to a subject's eye;
a control unit configured to sweep a wavelength of light emitted from the light source;
an imaging optical system configured to guide to an imaging unit a return beam from the subject's eye of light swept by the control unit;
a tomographic image acquisition unit configured to acquire a tomographic image of the subject's eye based on an output from the imaging unit;
a fundus image acquisition unit configured to acquire a fundus image of the subject's eye; and
a display control unit configured to display the fundus image in a first area in a display unit and display the tomographic image in a second area in the display unit which is different from the first area, wherein the display control unit changes a size of the second area in accordance with a viewing angle of the tomographic image, wherein the display control unit changes the horizontal width of the second area in accordance with a viewing angle of the tomographic image.

17. The ophthalmologic apparatus according to claim 16, wherein the display control unit reduces the horizontal width of the second area in a case where the viewing angle of the tomographic image is less than a predetermined value.

18. An ophthalmologic apparatus comprising:
an irradiation optical system configured to guide light emitted from a light source to a subject's eye;
an imaging optical system configured to guide to an imaging unit a return beam from the subject's eye of light guided by the irradiation optical system;
a tomographic image acquisition unit configured to acquire a tomographic image of the subject's eye based on an output from the imaging unit;
a fundus image acquisition unit configured to acquire a fundus image of the subject's eye; and
a display control unit configured to display the fundus image in a first area in a display unit and display the tomographic image in a second area in the display unit which is different from the first area, wherein the display control unit changes a size of the second area in accordance with a viewing angle of the tomographic image, wherein the display control unit changes the horizontal width of the second area in accordance with a viewing angle of the tomographic image.

19. The ophthalmologic apparatus according to claim 18, wherein the display control unit reduces the horizontal width of the second area in a case where the viewing angle of the tomographic image is less than a predetermined value.

* * * * *